US007559930B2

(12) United States Patent
Allard et al.

(10) Patent No.: US 7,559,930 B2
(45) Date of Patent: Jul. 14, 2009

(54) SURGICAL TOOL AND METHOD WITH AN ACTUATION MECHANISM FOR CONTROLLING RECIPROCATION AND LOCKING OF AN ANTI-ROTATION MEMBER RELATIVE TO AN ENGAGEMENT MEMBER FOR FACILITATING POSITIONING OF AN INTERVERTEBRAL DEVICE

(75) Inventors: Randall N. Allard, Germantown, TN (US); Jason J. Eckhardt, Memphis, TN (US); Robert B. Rice, Southaven, MS (US)

(73) Assignee: Warsaw Orthopedic, Inc.

( * ) Notice: Subject to any disclaimer, the term of this patent is extended or adjusted under 35 U.S.C. 154(b) by 471 days.

(21) Appl. No.: 11/340,277

(22) Filed: Jan. 26, 2006

(65) Prior Publication Data

US 2007/0191859 A1 Aug. 16, 2007

(51) Int. Cl.
*A61B 17/70* (2006.01)
*A61B 17/56* (2006.01)

(52) U.S. Cl. ....................................... 606/86 A; 606/99

(58) Field of Classification Search ............... 606/86 R, 606/86 A, 99

See application file for complete search history.

(56) References Cited

U.S. PATENT DOCUMENTS 5,885,299 A * 3/1999 Winslow et al. ............... 606/99
6,004,326 A 12/1999 Castro et al. .................. 606/99
6,074,423 A 6/2000 Lawson ....................... 623/17
6,083,225 A 7/2000 Winslow et al. ............... 606/61
6,200,322 B1 3/2001 Branch et al. ................. 606/96
6,224,607 B1 5/2001 Michelson ................... 606/96
6,290,724 B1 9/2001 Marino .................... 623/17.11
6,423,095 B1 7/2002 Van Hoeck et al. ...... 623/17.16
6,562,041 B1 5/2003 Yonemura et al. ............. 606/61
6,610,089 B1 8/2003 Liu et al. ................. 623/17.11
6,709,439 B2 3/2004 Rogers et al. ............... 606/100
6,733,535 B2 5/2004 Michelson ............... 623/17.16
6,805,716 B2 * 10/2004 Ralph et al. .............. 623/17.16
7,278,995 B2 * 10/2007 Nichols et al. .............. 606/272

(Continued)

FOREIGN PATENT DOCUMENTS

JP 7-163582 6/1995

OTHER PUBLICATIONS

Allard et al., "Non-Circular Stabilization Sphere and Method", U.S. Appl. No. 11/098,167, filed Apr. 4, 2005.

*Primary Examiner*—Eduardo C Robert
*Assistant Examiner*—Ellen Rust

(57) ABSTRACT

A surgical tool and method are provided for positioning an intervertebral device between vertebral members. The tool includes an elongate shaft, an anti-rotation sleeve, and an actuation mechanism. The shaft has proximal and distal ends, with the distal end of the shaft including an engagement member for releasably engaging an intervertebral device. The sleeve includes proximal and distal ends, and is movably mounted to the shaft for reciprocating relative thereto between retracted and extended positions. The distal end of the sleeve includes an anti-rotation member. The actuation mechanism controls positioning of the sleeve between the retracted and extended positions, and locks the sleeve relative to the shaft. When the intervertebral device is releasably engaged by the engagement member, and the sleeve is in the extended position, the anti-rotation member engages the intervertebral device and prevents rotation of the intervertebral device when releasing the engagement member from the intervertebral device.

14 Claims, 10 Drawing Sheets

812 810 805 800 822 820 842 850 855 840 852

U.S. PATENT DOCUMENTS

2002/0032448 A1 3/2002 Houfburg .................... 606/99
2002/0058950 A1 5/2002 Winterbottom et al. ....... 606/99
2002/0116006 A1 8/2002 Cohen ......................... 606/99
2003/0135275 A1 7/2003 Garcia et al. ............. 623/17.11
2003/0135276 A1 7/2003 Eckman ................... 623/17.11
2003/0135278 A1 7/2003 Eckman ................... 623/17.14
2004/0059337 A1 3/2004 Hanson et al. ................ 606/79
2004/0106996 A1 6/2004 Liu et al. ................. 623/17.11
2004/0147937 A1 7/2004 Dunbar, Jr. et al. ........... 606/99
2004/0267275 A1 12/2004 Cournoyer et al. ............ 606/99
2005/0010294 A1 1/2005 Michelson ............... 623/17.11
2005/0021041 A1 1/2005 Michelson ................... 606/90
2005/0027300 A1 2/2005 Hawkins et al. ............... 606/86
2005/0060035 A1 3/2005 Errico et al. ............. 623/17.15
2005/0090824 A1 4/2005 Shluzas et al. ................ 606/61
2005/0113920 A1 5/2005 Foley et al. .............. 623/17.11
2005/0131420 A1* 6/2005 Techiera et al. ............... 606/99
2005/0137593 A1 6/2005 Gray et al. .................... 606/61
2005/0149036 A1 7/2005 Varieur et al. ................. 606/86
2005/0149191 A1 7/2005 Cragg et al. ............. 623/17.11
2005/0165406 A1 7/2005 Assell et al. .................. 606/86
2005/0192671 A1 9/2005 Bao et al. ................ 623/17.14
2005/0209693 A1 9/2005 Lo et al. .................. 623/17.11
2005/0256575 A1 11/2005 Pavlov et al. ............ 623/17.11
2005/0273167 A1 12/2005 Triplett et al. ............ 623/17.11
2006/0004455 A1 1/2006 Leonard et al. .......... 623/17.15
2006/0241761 A1* 10/2006 Gately ..................... 623/17.11

* cited by examiner 855
852
850
842
840
820
822
800
805
810
812

855
927
927
850
925
840
920
842
950
844
960
940
805
800
900
910
812
912

SURGICAL TOOL AND METHOD WITH AN ACTUATION MECHANISM FOR CONTROLLING RECIPROCATION AND LOCKING OF AN ANTI-ROTATION MEMBER RELATIVE TO AN ENGAGEMENT MEMBER FOR FACILITATING POSITIONING OF AN INTERVERTEBRAL DEVICE

CROSS-REFERENCE TO RELATED APPLICATION

This application contains subject matter which is related to the subject matter of the following application, which is assigned to the same assignee as this application and which is hereby incorporated herein by reference in its entirety:

"Non-Circular Stabilization Sphere and Method", Allard et al., Ser. No. 11/098,167, filed Apr. 4, 2005.

TECHNICAL FIELD

The present invention relates generally to the field of surgery and medical implants, and more particularly, to surgical tools and methods for positioning an intervertebral device between vertebral members of a patient.

BACKGROUND OF THE INVENTION

The human spine is a biomechanical structure with thirty-three vertebral members, and is responsible for protecting the spinal cord, nerve roots and internal organs of the thorax and abdomen. The spine also provides structure support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

Procedures to remedy back problems sometimes require correcting the distance between vertebral members by inserting an intervertebral device (e.g., spacer) between the members. The spacer, which is carefully positioned within the disc space and aligned relative to the vertebral members, is sized to position the vertebral members in a manner to alleviate the patient's back pain.

Further, the intervertebral device is preferably designed to facilitate insertion into a patient. That is, the shape and size of the device are designed to provide for minimal intrusion to a patient during insertion, but still be effective post-insertion to alleviate the pain and provide maximum mobility to the patient.

SUMMARY OF THE INVENTION

The present invention comprises an insertion tool and method for facilitating positioning an intervertebral device (e.g., spacer) within the body. The tools and methods disclosed herein employ a tool-to-device attachment approach that is of sufficient strength for the insertion tool to be readily utilized to accurately insert and place the device. Further, the attachment approach provides for detachment and removal of the insertion tool while the intervertebral device remains within the body, and does not deter from the functionality of the device once within the body.

More particularly, in one aspect, presented herein is a surgical tool for positioning an intervertebral device between vertebral members of a patient. The surgical tool includes an elongate shaft and an anti-rotation sleeve. The elongate shaft has proximal and distal ends which define a longitudinal axis extending therebetween. The distal end of the elongate shaft includes an engagement member adapted to releasably engage the intervertebral device. The anti-rotation sleeve, which includes proximal and distal ends, is movably mounted to the elongate shaft and reciprocates relative thereto between a retracted position and an extended position. The distal end of the anti-rotation sleeve includes an anti-rotation member. The surgical tool further includes an actuation mechanism for controlling positioning and reciprocation of the anti-rotation sleeve relative to the elongate shaft between the retracted position and the extended position. When the intervertebral device is releasably engaged by the engagement member at the distal end of the elongate shaft and the anti-rotation sleeve is in the extended position, the anti-rotation member at the distal end of the anti-rotation sleeve engages the intervertebral device and prevents rotation of the intervertebral device when releasing the engagement member from engagement with the intervertebral device.

In another aspect, the surgical tool presented herein includes an elongate shaft, an impaction cap, and an elongate anti-rotation sleeve. The elongate shaft has proximal and distal ends which define a first longitudinal axis extending therebetween. The distal end of the elongate shaft includes a threaded engagement member adapted to releasably engage the intervertebral device. The impaction cap is physically connected to the proximal end of the elongate shaft so that impacting force applied to the impaction cap is transferred to the elongate shaft, and hence to the threaded engagement member at the distal end thereof. The elongate anti-rotation sleeve includes proximal and distal ends which define a second longitudinal axis extending therebetween. The second longitudinal axis of the elongate anti-rotation sleeve is coaxial with the first longitudinal axis of the elongate shaft. The elongate anti-rotation sleeve is movably mounted to the elongate shaft and reciprocates relative thereto between a retracted position and an extended position. The distal end of the elongate anti-rotation sleeve includes an anti-rotation member. The surgical tool further includes an actuation mechanism for controlling positioning and reciprocation of the elongate anti-rotation sleeve relative to the elongate shaft between the retracted position and the extended position, and for locking the elongate anti-rotation sleeve relative to the elongate shaft. When the intervertebral device is releasably engaged by the threaded engagement member at the distal end of the elongate shaft, and the elongate anti-rotation sleeve is in the extended position, the anti-rotation member at the distal end of the elongate anti-rotation sleeve engages the intervertebral device and prevents rotation of the intervertebral device when releasing the threaded engagement member from engagement with the intervertebral device.

In a further aspect, a method of positioning an intervertebral device between vertebral members of a patient is provided. The method includes employing a surgical tool having: an elongate shaft with proximal and distal ends defining a longitudinal axis extending therebetween, the distal end of the elongate shaft comprising an engagement member adapted to releasably engage the intervertebral device; an elongate anti-rotation sleeve having proximal and distal ends, the elongate anti-rotation sleeve being movably mounted to the elongate shaft and reciprocating relative thereto between a retracted position and an extended position, the distal end of the elongate anti-rotation sleeve comprising an anti-rotation member; and an actuation mechanism for controlling positioning and reciprocation of the elongate anti-rotation sleeve relative to the elongate shaft between the retracted and extended positions, and for locking the elongate anti-rotation sleeve relative to the elongate shaft. The employing of the surgical tool comprises: employing the engagement member at the distal end of the elongate shaft of the surgical tool to releasably engage the intervertebral device; employing the actuation mechanism of the surgical tool to position the elongate anti-rotation sleeve in the extended position to engage the intervertebral device, and to lock the elongate anti-rotation sleeve relative to the elongate shaft; inserting the intervertebral device between the vertebral members of a patient employing the surgical tool; releasing the engagement member at the distal end of the elongate shaft from engagement with the intervertebral device; and thereafter, retracting the anti-rotation member from engagement with the intervertebral device.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

BEST MODE FOR CARRYING OUT THE INVENTION

Generally stated, disclosed herein are various surgical inserter tools and methods for facilitating positioning of an intervertebral device between vertebral members of a patient. The intervertebral device may comprise a spacer having any one of various spherical, non-spherical, oblong, etc. shapes. By way of example, one non-spherical-shaped embodiment of a spacer, disclosed in the above-incorporated patent application entitled "Non-Circular Stabilization Sphere and Method" is described below with reference to FIGS. 1-4.

Figure 1:
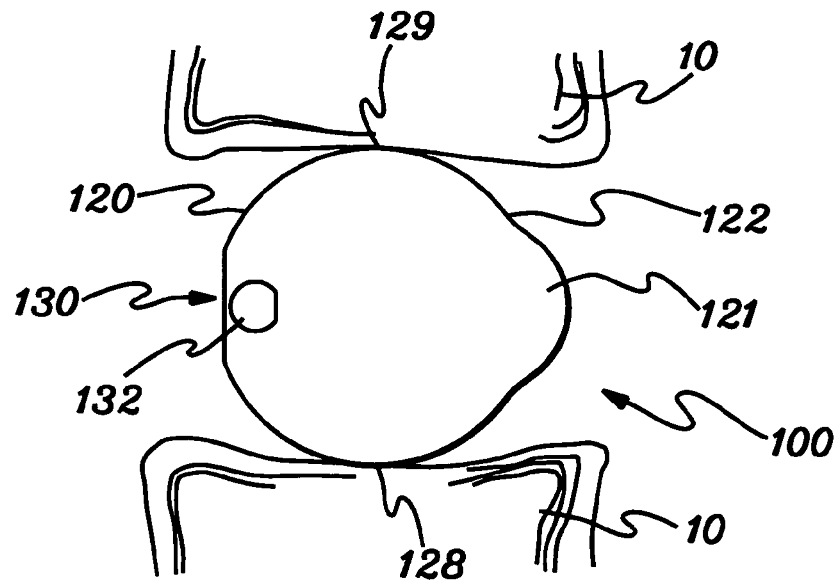
FIG. 1 is a side view of one embodiment of an intervertebral device positioned between two vertebral members, in accordance with an aspect of the present invention.

As shown in FIG. 1, the spacer 100, inserted between first and second vertebral members 10, has an overall non-spherical shape defined by a first section 120 and a second section 121. First and section sections 120, 121 are arranged in an overlapping orientation to give spacer 100 its overall non-spherical shape. An attachment opening 130, located within one of first and second sections 120, 121, is at a position within the spacer to remain spaced away from and avoid contact with vertebral members 10.

Figure 1A:
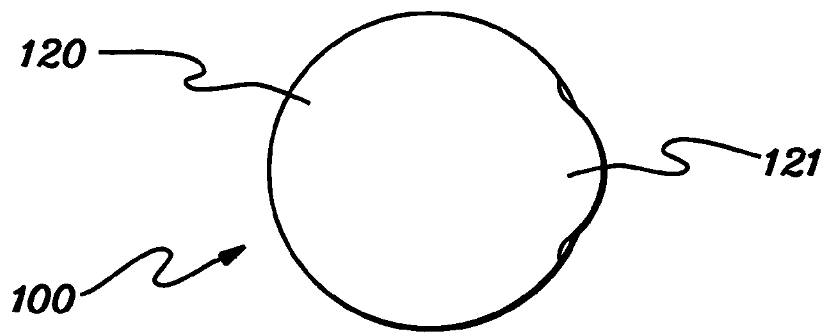
FIG. 1A is a perspective view of the intervertebral device of FIG. 1, in accordance with an aspect of the present invention.
Figure 2:
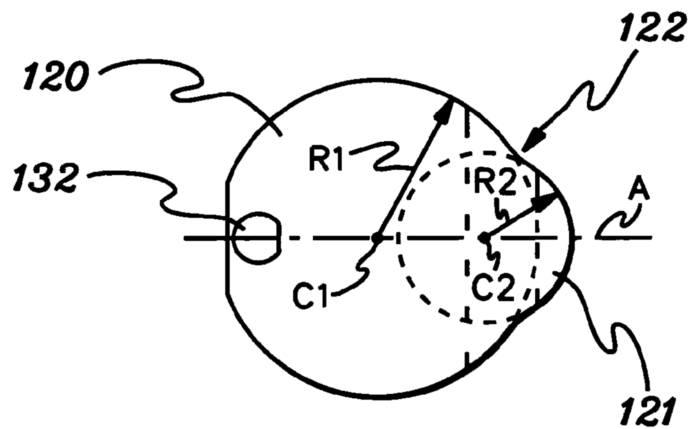
FIG. 2 is a side elevational view of the intervertebral device of FIGS. 1 & 1A, in accordance with an aspect of the present invention.

The non-spherical shape of spacer 100 facilitates maintaining the orientation of spacer 100 with the inferior 128 and superior 129 surfaces thereof in contact with the vertebral members 10. As shown in FIGS. 1A & 2, first section 120 forms a majority of spacer 100 and has a larger surface area that second section 121. First section 120 is substantially spherical having a radius R1 (see FIG. 2) that extends from a center point C1. Second section 121 extends outward in a first direction from first section 120. In this embodiment, second section 121 is positioned on the anterior side of first section 120, and is substantially spherical having a radius R2 that extends from a center point C2. Both center points C1 and C2 are aligned along a common centerline A.

FIG. 2 illustrates the exterior surface of spacer 100 in solid lines. The dashed lines illustrate the overlapping area between first and second sections 120, 121. In one embodiment, first and second sections 120, 121 are aligned with an overall length of the spacer 100 being about 9.6 mm. A transition section 122 is positioned along an area where the exterior surface of first section 120 merges with the exterior surface of second section 121. The protrusion of second section 121 with respect to first section 120 may cause transition section 122 to be convex (as illustrated in FIG. 2), tangent, or concave.

Figure 3:
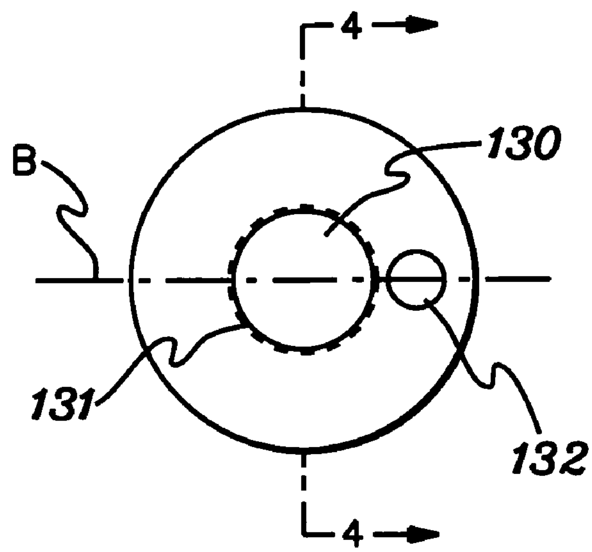
FIG. 3 is an end elevational view of the intervertebral device of FIGS. 1, 1A & 2, in accordance with an aspect of the present invention.
Figure 4:
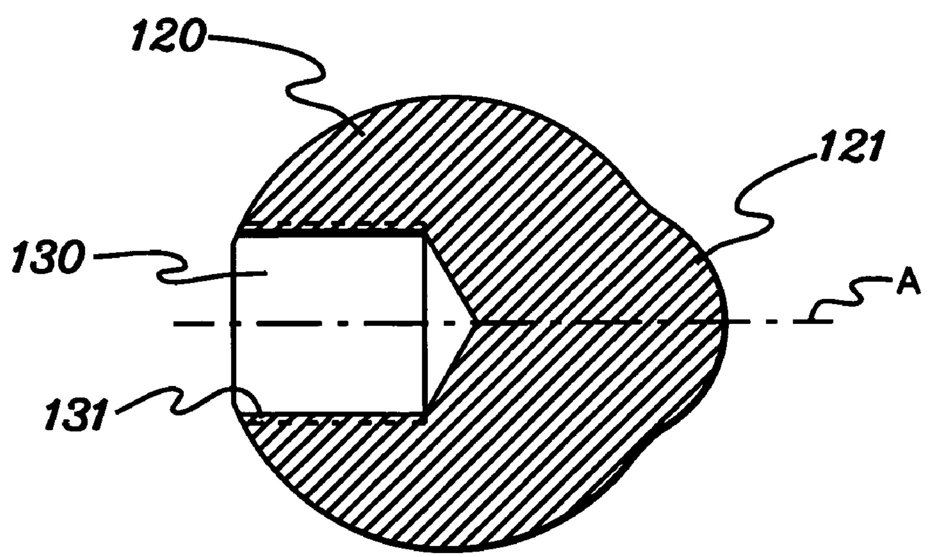
FIG. 4 is a cross-sectional elevational view of the intervertebral device of FIG. 3, taken along line A-A, in accordance with an aspect of the present invention.

As shown in FIGS. 3 & 4, an attachment opening 130 includes threads 131 for releasable engagement by a surgical insertion tool. Attachment opening 130 is centered on longitudinal centerline A, and a lateral centerline B within spacer 100. In one embodiment, the depth of opening 130 is about 3.7 mm. An anti-rotation opening 132 also extends into spacer 100, and is positioned in proximity to attachment opening 130. Anti-rotation opening 132 interacts with an anti-rotation member (e.g., a correspondingly shaped pin) in the surgical insertion tool (described below) to facilitate positioning of spacer 100. Opening 130 and anti-rotation opening 132 are positioned in spacer 100 at an end thereof, away from vertebral members 10. In the illustration of FIG. 1, openings 130 & 132 are located on the posterior section of spacer 100. The non-spherical shape of spacer 100 again facilitates maintaining the superior 129 and inferior 128 surfaces of the first section 120 in contact with vertebral members 10, and the attachment features, i.e., openings 130 & 132, away from the vertebral members 10.

By way of example, when spacer 100 rotates in a first direction (clockwise), a lower surface of second section 121 contacts the lower vertebral member to prevent contact of openings 130 & 132 with the upper vertebral member. When spacer 100 rotates in a second direction (counter-clockwise), an upper surface of second section 121 contacts the upper vertebral member to prevent the openings 130, 132 from contacting the lower vertebral member.

Those skilled in the art should note that the term "vertebral member" is used generally herein to describe the vertebral geometry comprising the vertebral body, pedicles, lamina, and processes. Likewise, the term "intervertebral space" is used generally to describe the space between vertebral members. The intervertebral space may be formed between adjacent vertebral members, or between non-adjacent vertebral members. The intervertebral device, e.g., spacer 100, may be sized and shaped, and have adequate strength requirements to be used within the different regions of the spine. Although the devices and methods illustrated and described above are particularly useful in treating the lumbar region of the spine, it should nevertheless be understood that the intervertebral device may be positioned in other portions of the spine, including the cervical, thoracic, and sacro-iliac regions.

The embodiment of FIGS. 1-4 is illustrated with first section 120 having a substantially flat section opposite from second section 121. In one embodiment, the attachment opening 130 is positioned within this flat section. In other embodiments, the first section 120 does not include a flat or substantially flat section. Further, note that the device embodiment disclosed herein by way of example includes the attachment opening 130 and anti-rotation opening 132 positioned within a posterior section of spacer 100. This placement provides for a posterior insertion approach. It is to be understood that these elements may also be positioned at other locations on spacer 100, such as in an anterior section for an anterior insertion approach, or along a lateral edge for a lateral approach. In each embodiment, the position of these openings is such that they are spaced from vertebral members 10 (see FIG. 1) to prevent damage.

The term "spacer 100" is used herein in a general sense to describe an intervertebral device that is positioned between vertebral members. In one embodiment, spacer 100 is an implant that remains within the body. In another embodiment, spacer 100 is a jib which is a fixture or device to guide or hold a cutting, measuring, or space maintaining device in order to prepare a location, such as a vertebral member or intervertebral space, in order to receive an implant. In these embodiments, spacer 100 may be removed from the body at the completion of the procedure.

Other intervertebral device embodiments may be carried out in other specific ways than those herein set forth without departing from the scope of the present invention. The terms "upper", "lower", "inner", "outer", and the like are terms to describe the relative positioning of different elements, and are used in a general sense. Spacer 100 may be solid, as illustrated in FIG. 4, or have a hollow interior. Openings 130 & 132 may have different depths and varying diameters. The intervertebral device embodiments discussed are, therefore, to be considered in all respects as illustrative and not restrictive, and all changes coming within the meaning and equivalency range of the appended claims are intended to be embraced therein.

FIGS. 5-16 depict various embodiments of a surgical inserter tool for securely engaging, inserting in an intervertebral space and disengaging an intervertebral device (such as spacer 100 depicted above in connection with FIGS. 1-4). In each of the embodiments described below, the surgical tool includes an actuation mechanism for controlling positioning and reciprocation of an anti-rotation sleeve relative to an elongate shaft between retracted and extended positions, and for locking the anti-rotation sleeve relative to the elongate shaft. Advantageously, the actuation mechanism locks the anti-rotation sleeve relative to the elongate shaft notwithstanding impaction of the surgical tool, for example, during insertion of an intervertebral device between vertebral members of a patient.

Figure 5:
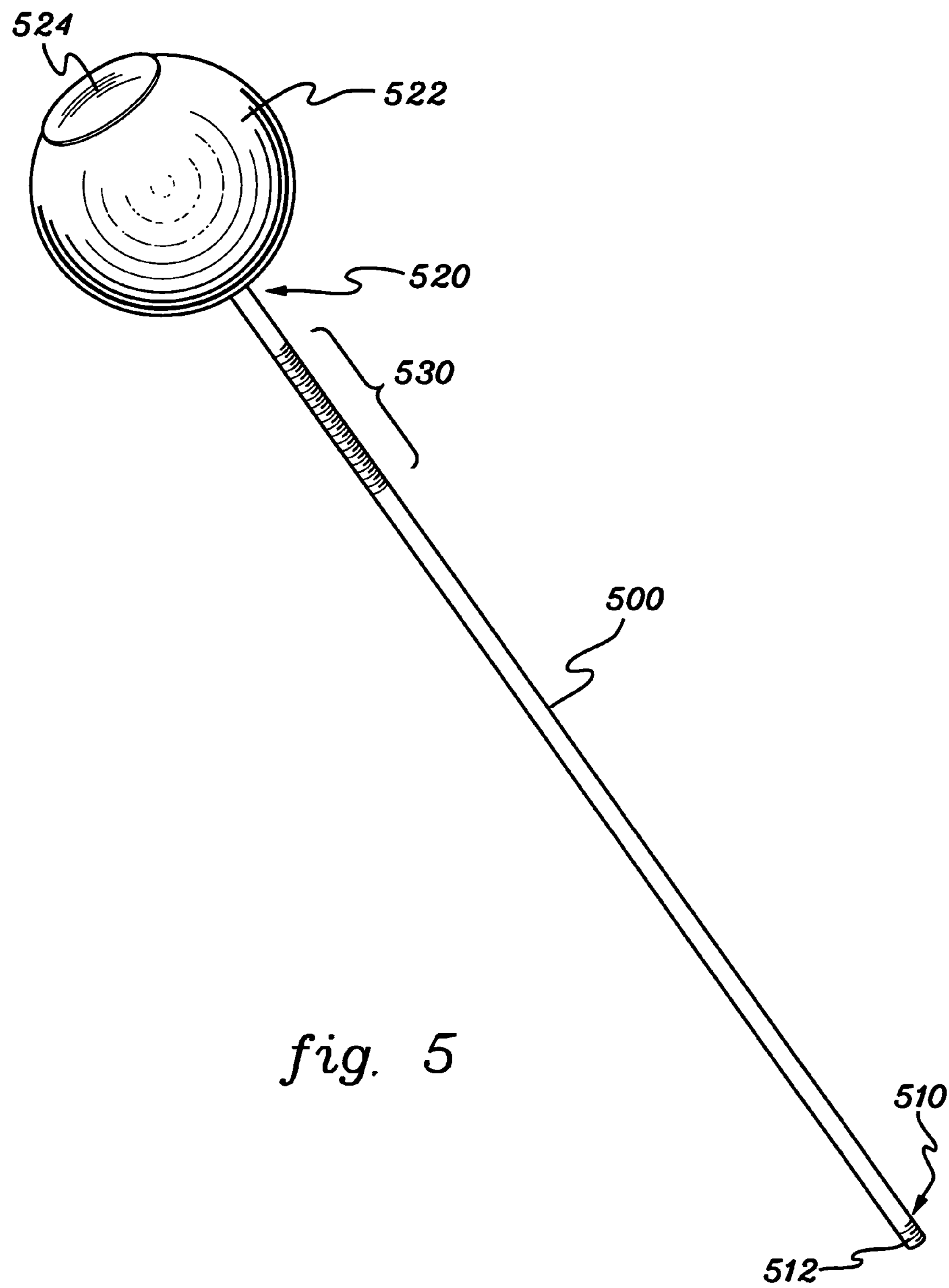
FIG. 5 is an isometric view of one embodiment of an elongate shaft having an engagement member and a handle with an impaction cap coupled thereto, in accordance with an aspect of the present invention.
Figure 6:
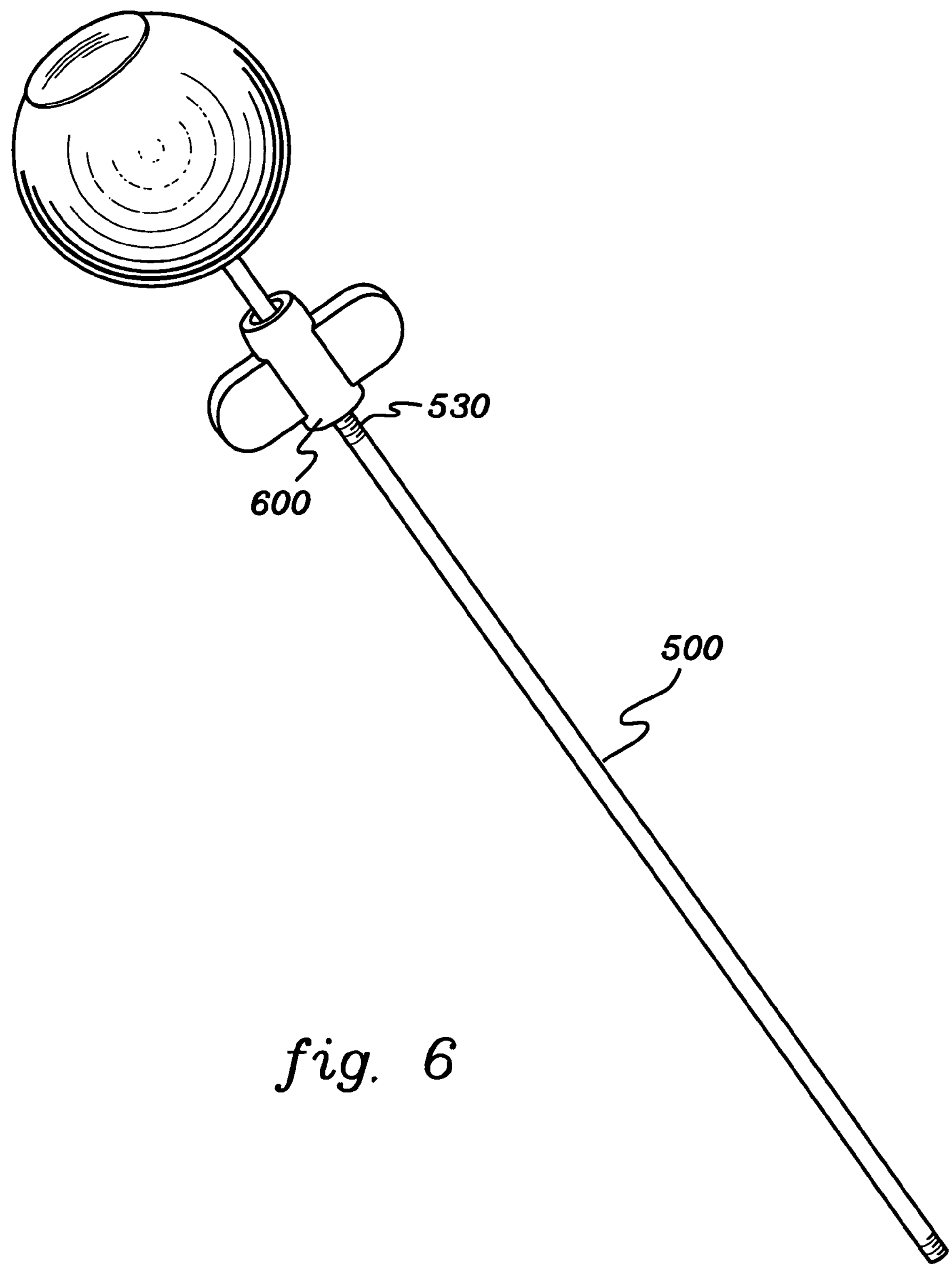
FIG. 6 is an isometric view of the elongate shaft of FIG. 5, showing the addition of an actuation mechanism comprising a threaded collar, in accordance with an aspect of the present invention.
Figure 7:
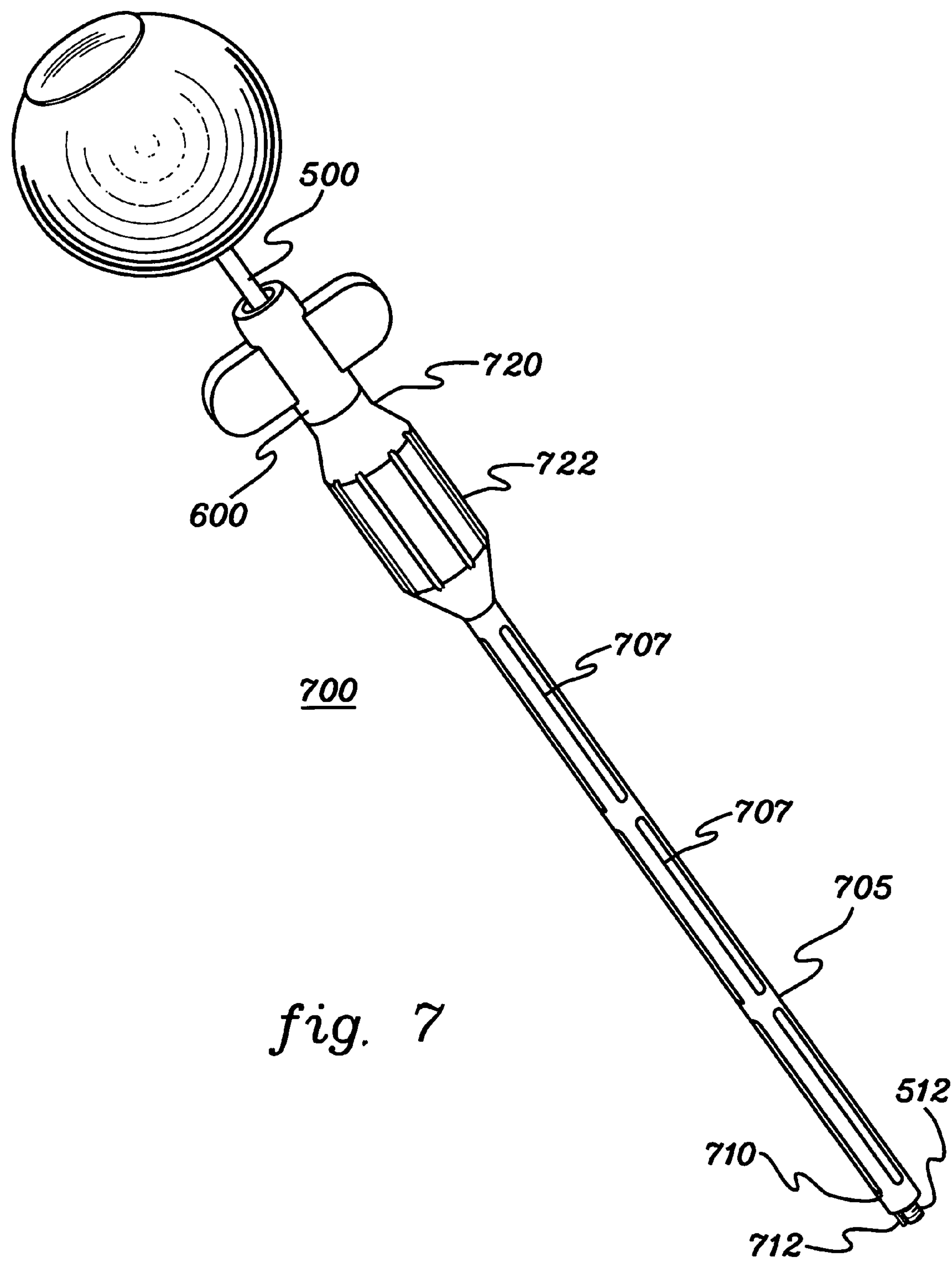
FIG. 7 is an isometric view of one embodiment of a surgical tool comprising the elongate shaft and actuation mechanism of FIG. 6, and an elongate sleeve (with an anti-rotation member) movably mounted to the elongate shaft, in accordance with an aspect of the present invention.

A first embodiment of a surgical inserter tool, in accordance with an aspect of the present invention, is illustrated in FIGS. 5-7 and described below.

As shown in FIG. 5, an elongate inserter shaft 500 has a distal end 510 and a proximal end 520 defining a longitudinal axis extending therebetween. Distal end 510 of elongate inserter shaft 500 includes an engagement member 512 adapted to releasably engage an intervertebral device. In this embodiment, member 512 is shown by example to be a threaded member, which is sized to attach a threaded opening in the intervertebral device to be releasably engaged (e.g., opening 130 of spacer 100 illustrated in FIGS. 1-4). A handle 522 is mounted to proximal end 520 of inserter shaft 500 to facilitate manipulation of the surgical tool. Since handle 520 may comprise a non-metallic material, such as plastic or rubber, a metal inserter cap 524 is provided mechanically coupled to elongate inserter shaft 500 (which in one embodiment is also fabricated of metal) to allow the application of impacting force to the shaft, and hence to an intervertebral device attached to the distal end 510 of the shaft. A threaded region 530 is also provided on elongate shaft 500 adjacent to proximal end 520 thereof.

As shown in FIG. 6, the actuation mechanism for this embodiment of the surgical tool comprises a threaded collar 600 sized to threadably mount to threaded region 530 of elongate shaft 500.

FIG. 7 depicts one embodiment of the assembled surgical inserter tool, generally denoted 700, wherein an anti-rotation sleeve 705 is shown moveably mounted over the elongate inserter shaft 500. Anti-rotation sleeve 705 includes a distal end 710 and proximal end 720. Distal end 710 includes an anti-rotation member 712 extending along an axis parallel with the axis of engagement member 512 at the distal end of inserter shaft 500. Proximal end 720 of sleeve 705 is engaged by locking collar 600. Collar 600 controls positioning and reciprocation of the anti-rotation sleeve relative to the inserter shaft between a retracted position and an extended position, and functions to lock the elongate anti-rotation sleeve relative to the inserter shaft. In this example, anti-rotation sleeve 705 further includes slots 707 (for example, to facilitate cleaning and sterilization of the surgical tool), and a grip 722 formed therein at the proximal end 720 to facilitate handling of the anti-rotation sleeve.

FIGS. 8-12 depict a second embodiment of a surgical tool, in accordance with an aspect of the present invention.

Figures 8, 9:
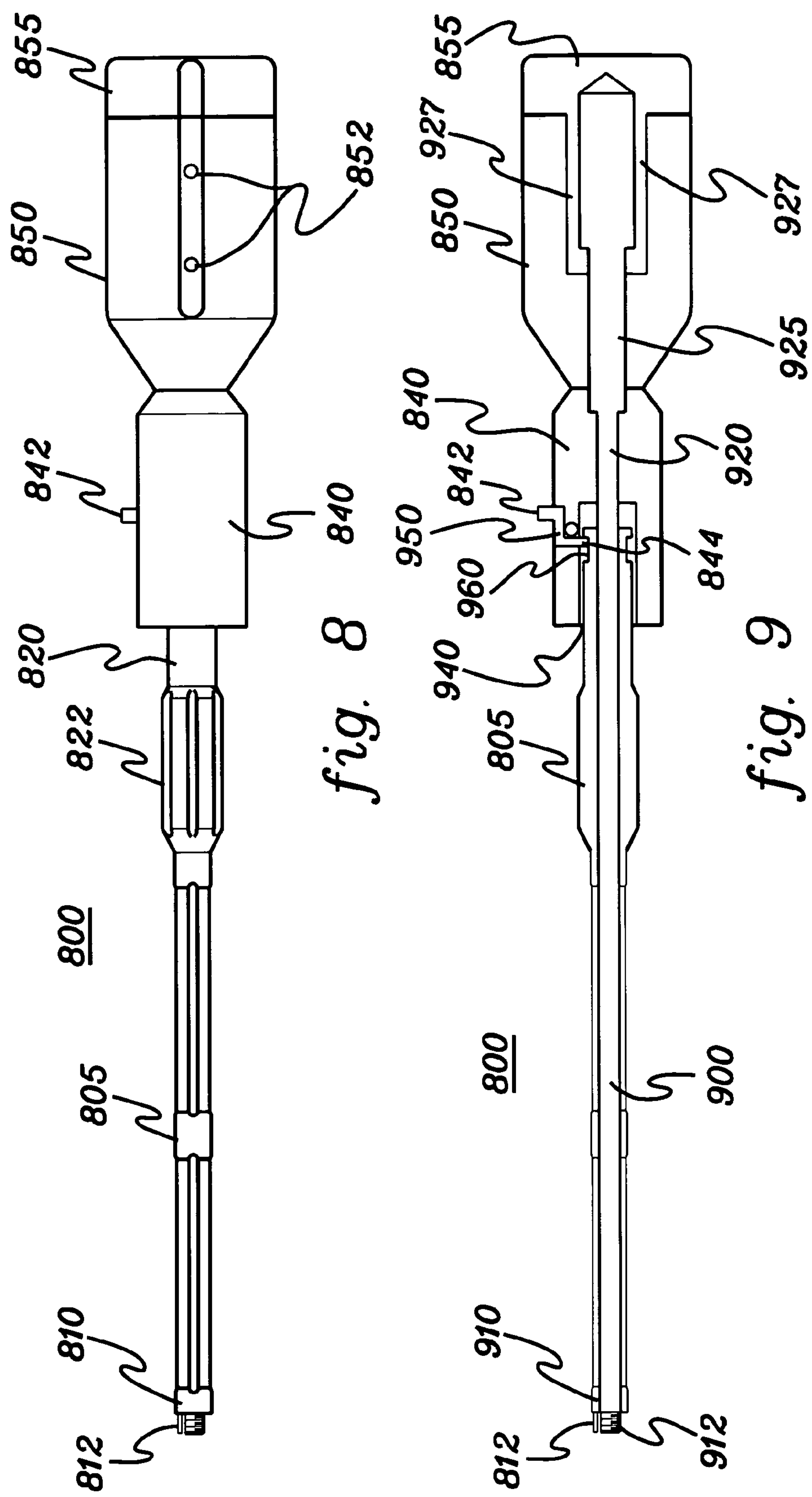
FIG. 8 is a side elevational view of another embodiment of a surgical tool, in accordance with an aspect of the present invention.
FIG. 9 is a cross-sectional elevational view of the surgical tool of FIG. 8, in accordance with an aspect of the present invention.
Figure 10:
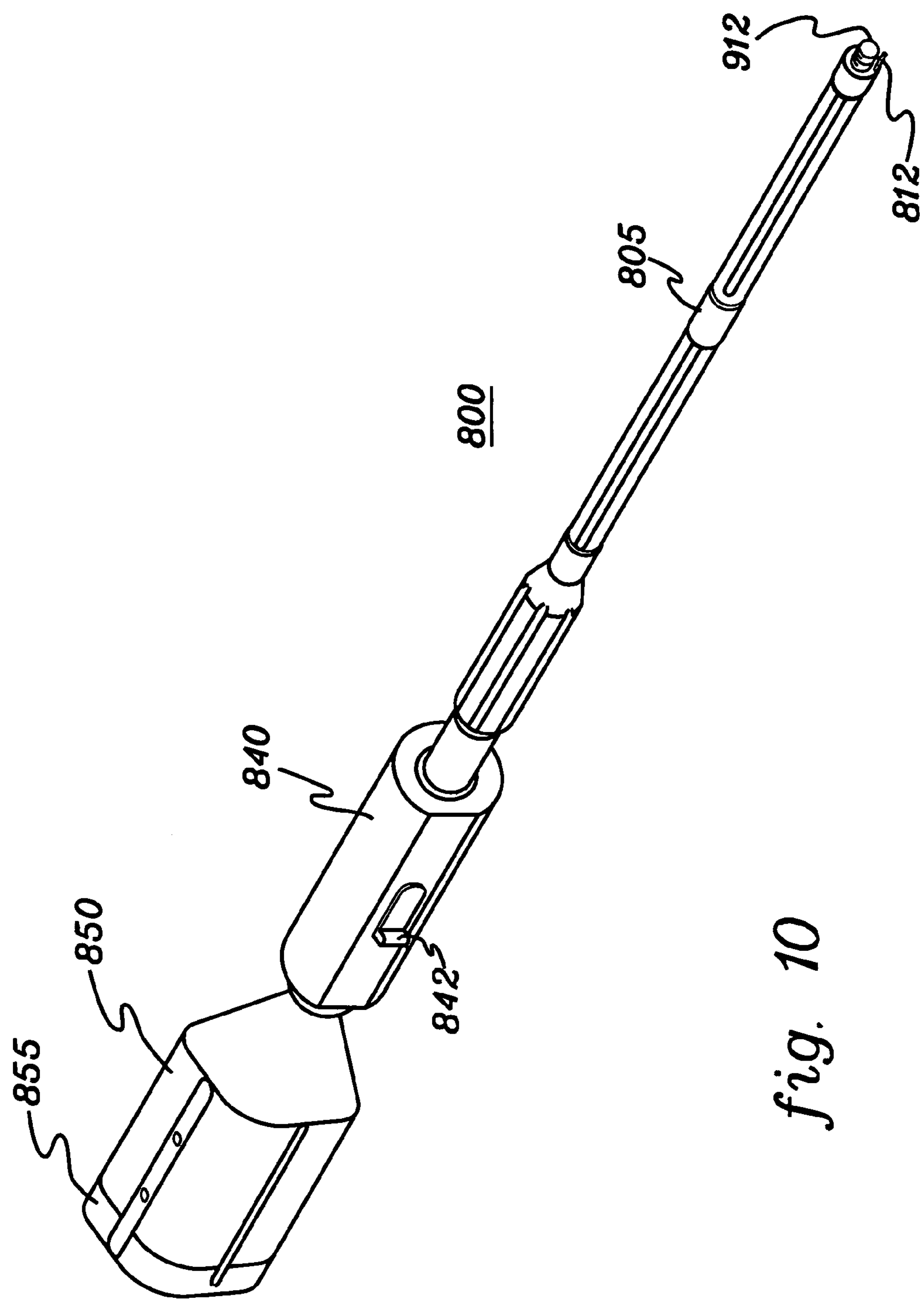
FIG. 10 is an isometric view of the surgical tool of FIGS. 8 & 9, in accordance with an aspect of the present invention.

Referring first to FIGS. 8-10, one embodiment of the surgical tool, generally denoted 800, is illustrated. In this embodiment, an inserter shaft 900 (see FIG. 9) again includes a distal end 910 and a proximal end 920 with a longitudinal axis extending therebetween. Distal end 910 includes an engagement member 912, such as a threaded member, for engaging an intervertebral device as described above. Shaft 900 steps at proximal end 920 to wider diameter shafts 925 within a handle 850 to facilitate secure coupling of the shaft to an impaction cap 855. Impaction cap 855 may include a cylindrical portion 927 configured and sized to mate to stepped-out shaft 925 at the proximal end 920 of the shaft. Press fit pins 852 are included extending through handle 850, cylindrical portion 927 of impaction cap 855, and stepped-out shaft 925 to ensure secure attachment of the respective components.

This embodiment again includes an elongate anti-rotation sleeve 805 which is movably mounted to the elongate shaft 900. Sleeve 805 again includes a distal end 810 and proximal end 820. Distal end 810 has an anti-rotation member 812 extending therefrom in a direction parallel to threaded member 912 at the distal end 910 of shaft 900. Sleeve 805 is further formed with a grip 822 adjacent to proximal end 820 to facilitate handling of the anti-rotation sleeve.

As shown in FIG. 9, proximal end 820 of sleeve 805 reciprocates within an axial opening 940 in an actuation cover 840, which is fixedly secured to proximal end 920 of inserter shaft 900 adjacent to handle 850. In addition to actuation cover 840, the actuation mechanism of this surgical tool includes one or more spring-biased latch mechanisms, which are biased to lock the elongate anti-rotation sleeve relative to the elongate shaft, and when compressively engaged, allow for reciprocation of the elongate anti-rotation sleeve 805 relative to shaft 900 between a retracted and extended position. Each latch mechanism includes a spring-biased latch member 950 pivotally mounted within actuation cover 840. Each latch member includes a first end 842 comprising an exposed button, and a second end 844 configured to engage the anti-rotation sleeve in a groove 960 in the proximal end 820 of anti-rotation sleeve 805.

Figure 11:
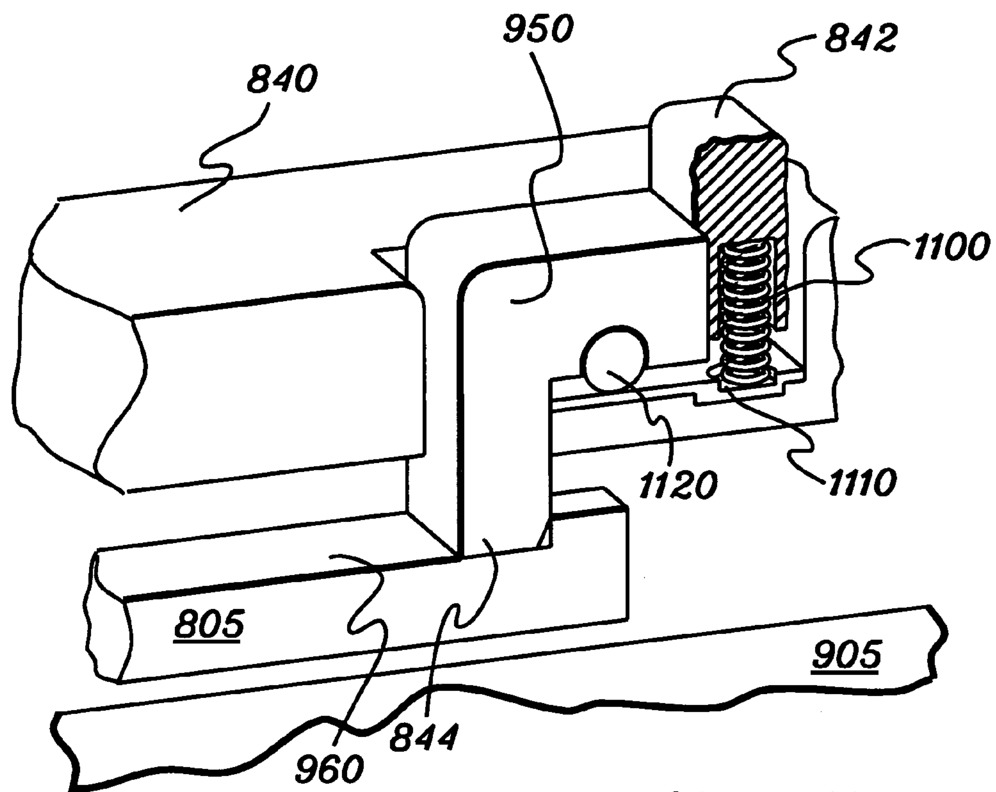
FIG. 11 is a partial cross-sectional isometric view of the surgical tool of FIGS. 8-10 showing an enlarged embodiment of a spring-biased latch mechanism employed by the surgical tool, in accordance with an aspect of the present invention.
Figure 12:
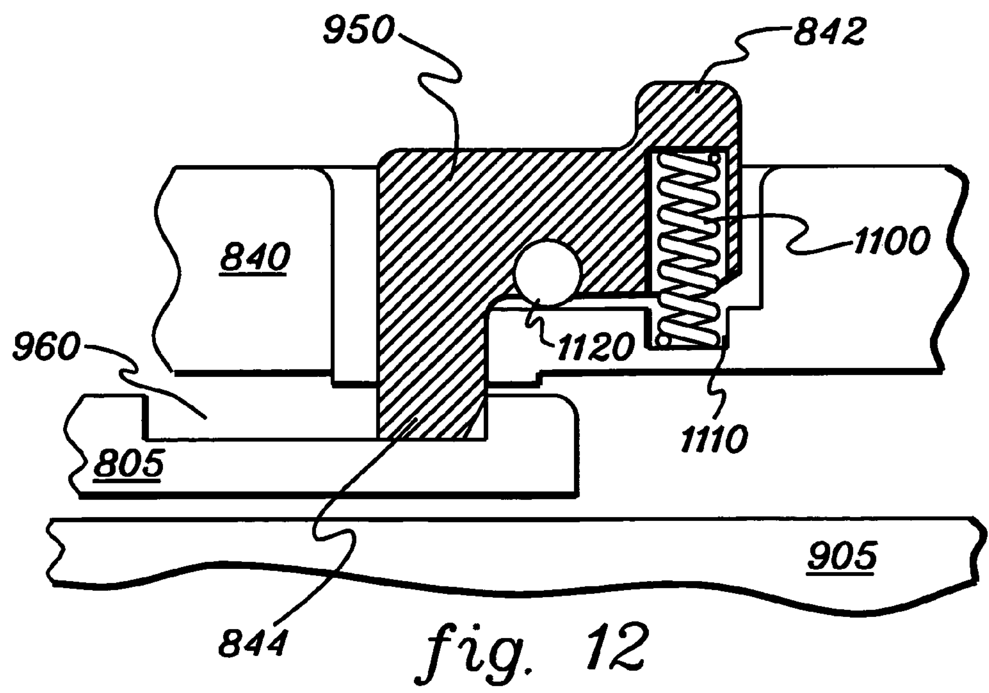
FIG. 12 is a cross-sectional elevational view of the spring-biased latch mechanism of FIG. 11, in accordance with an aspect of the present invention.

One embodiment of the above-described spring-biased latch mechanism is illustrated in greater detail in the enlarged depictions of FIGS. 11 & 12. As shown, each spring-biased latch member 950 is pivotally mounted 1120 within actuation cover 840, and is spring-biased 1100 at one end so that second end 844 of member 950 engages sleeve 805 in groove 960 at the proximal end thereof. Spring 1100 is seated 1110 in actuation cover 840.

In operation, when first end 842 of member 950 is downwardly compressively engaged, spring 1100 compresses, allowing pivoting of member 950 about pivot 1120 and raising of second end 844 of the member from engagement with sleeve 805. By lifting second end 844 from engagement with sleeve 805, reciprocation of sleeve 805 relative to shaft 905 is possible. When the downward compressive force is removed from first end 842 of member 950, spring biasing 1100 forces second end 844 back into engagement with sleeve 805, and thereby locks sleeve 805 relative to shaft 950. Note that in this embodiment, the length of groove 960 in sleeve 805 corresponds to the distance between the retracted and extended positions of the sleeve relative to the inserter shaft.

FIGS. 13-16 depict still another embodiment of a surgical tool, in accordance with an aspect of the present invention.

Figure 13:
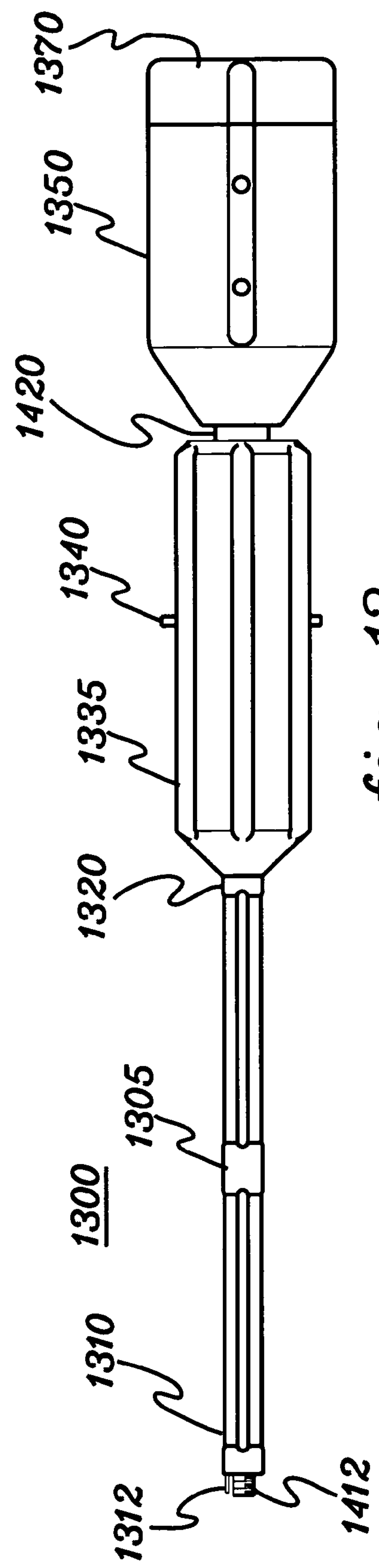
FIG. 13 is an elevational view of still another embodiment of a surgical tool, in accordance with an aspect of the present invention.
Figure 14:
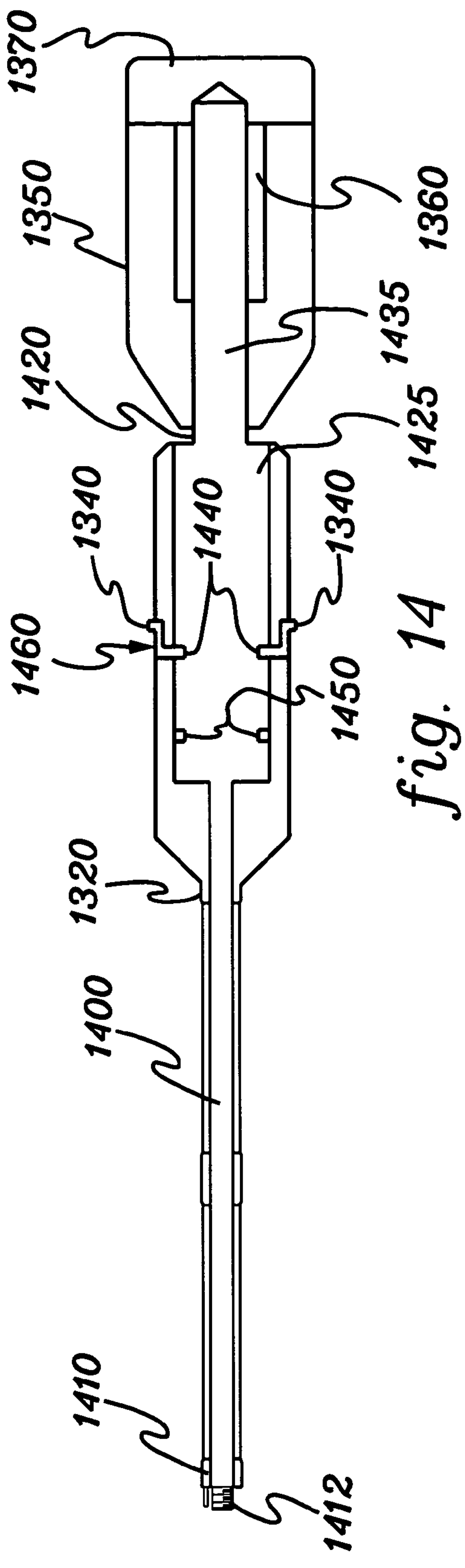
FIG. 14 is a cross-sectional elevational view of the surgical tool of FIG. 13, in accordance with an aspect of the present invention.
Figure 15:
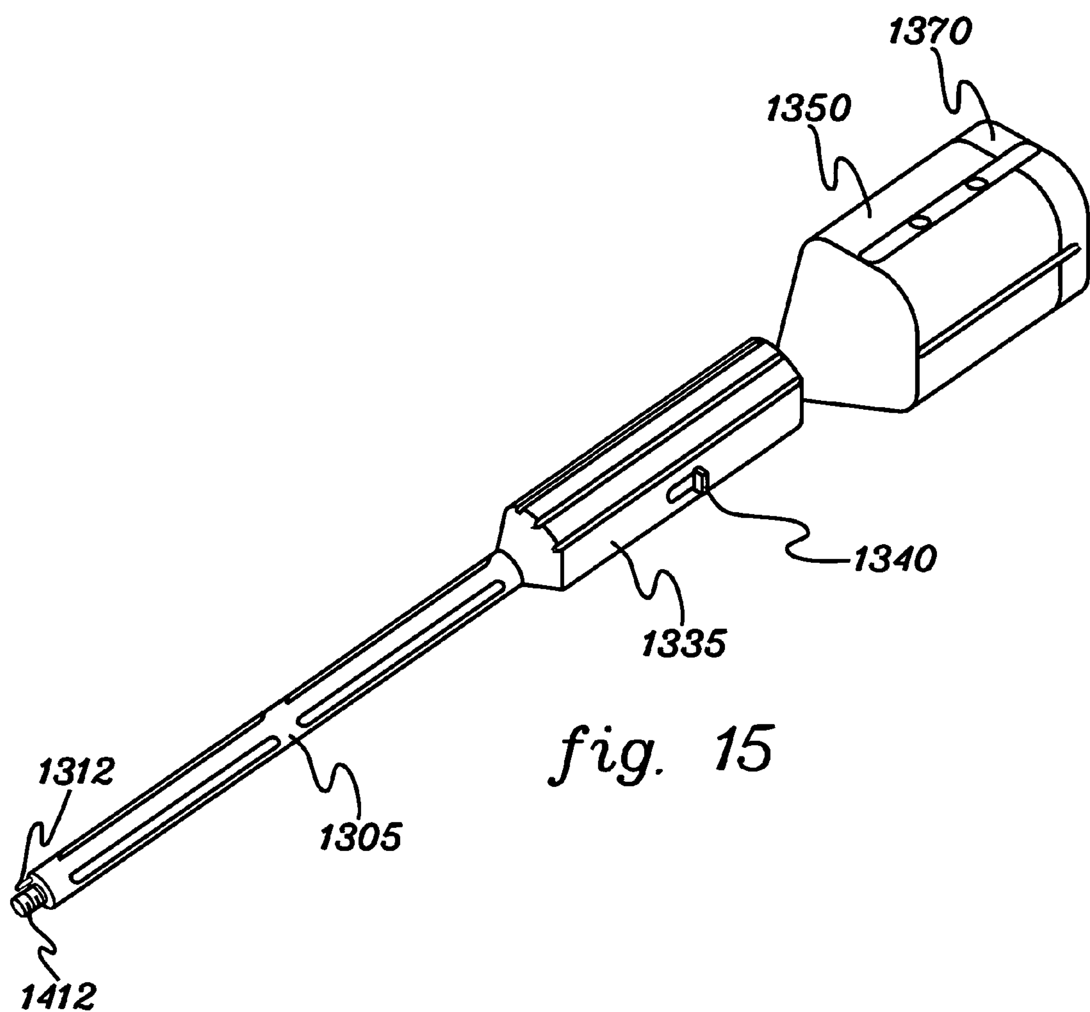
FIG. 15 is an isometric view of the surgical tool of FIGS. 13 & 14, in accordance with an aspect of the present invention.

Referring to FIGS. 13-15, the inserter tool, generally denoted 1300, includes an elongate anti-rotation sleeve 1305 movably mounted to an inserter shaft 1400. Sleeve 1305 includes distal end 1310 and proximal end 1320, while shaft 1400 includes distal end 1410 and proximal end 1420. Distal end 1310 of sleeve 1305 comprises an anti-rotation member 1312 such as described above for engagement with a corresponding anti-rotation opening in the intervertebral device being inserted between vertebral members of a patient. Distal end 1410 of shaft 1400 includes an engagement member 1412, such as a threaded member sized to threadably engage a corresponding threaded opening in the intervertebral device for secure attachment of the surgical tool to the intervertebral device.

In the illustrated embodiment, the actuation mechanism for this tool includes an actuation cover 1335 integrally formed with the proximal end 1320 of sleeve 1305. The proximal end 1420 of shaft 1400 includes a handle 1350 and an impaction cap 1370 mounted thereto in a manner similar to that described above in connection with surgical tool 800 of FIGS. 8-10.

In this tool embodiment, elongate inserter shaft 1400 includes a stepped-out shaft 1425 of larger diameter which resides at least partially within a center opening formed in actuation cover 1335, as well as an intermediate shaft diameter region 1435 within handle 1350 and mated to impaction cap 1370 via a cylindrical sleeve 1360 connected to cap 1370. At least two circumferential grooves 1440 & 1450 are provided in shaft region 1425 residing partially within the actuation cover 1335. The actuation mechanism includes, in this embodiment, two spring-biased latch mechanisms 1460, which are disposed 180 degrees apart about the shaft. Provision of two such latch mechanisms 1460 further ensures locking engagement of the sleeve relative to the shaft notwithstanding impacting of the tool at the impaction cap.

Figure 16:
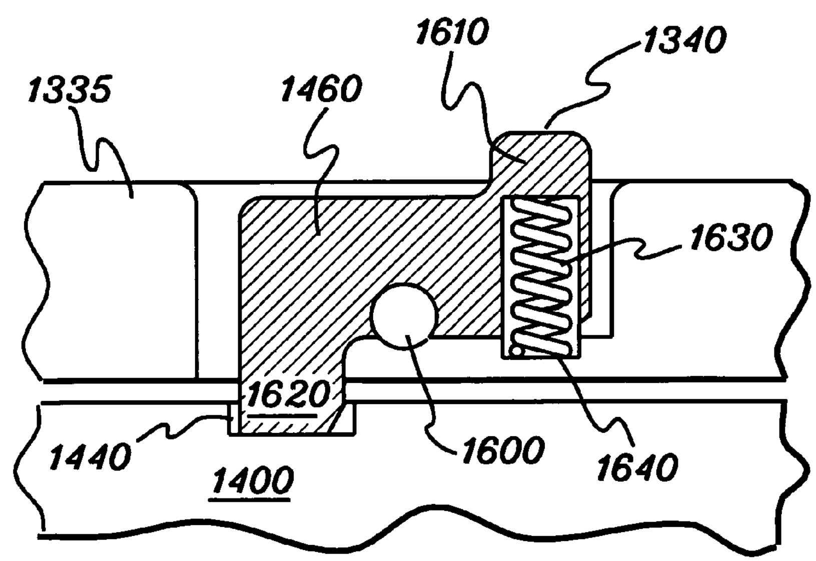
FIG. 16 is a partial cross-sectional elevational view of the surgical tool of FIGS. 13-15 showing one embodiment of a spring-biased latch mechanism employed in the surgical tool, in accordance with an aspect of the present invention.

One embodiment of latch mechanism 1460 is depicted in greater detail in FIG. 16. As shown, this embodiment of latch mechanism 1460 is similar to the latch mechanism described above in connection with FIGS. 11 & 12 for the surgical tool embodiment 800 of FIGS. 8-10. Referring to FIG. 16, latch mechanism 1460 is shown pivotally mounted 1600 to actuation cover 1335, and spring-biased 1630 at a first end 1610 to ensure engagement of a second end 1620 with shaft 1400, and more particularly, with one of the two or more circumferential grooves (such as groove 1440) provided in shaft 1400. As shown, spring-biasing 1630 is mounted within a seat 1640 provided in actuation cover 1335.

In operation, buttons 1340 at first end 1610 of the latch members are simultaneously compressed, thereby withdrawing member ends 1620 from engagement with shaft region 1425 and allowing reciprocation of sleeve 1305 relative to shaft 1400 between the retracted and extended positions, defined in this embodiment, by the distance between the two circumferential grooves provided in shaft 1400.

Positioning of an intervertebral device between vertebral members of a patient can be accomplished employing any one of the surgical tools illustrated in FIGS. 5-16 and described above. The insertion method includes employing a surgical tool characterized by: having an elongate shaft with proximal and distal ends defining a longitudinal axis extending therebetween, the distal end of the elongate shaft including an engagement member adapted to releasably engage the intervertebral device; an elongate anti-rotation sleeve having proximal and distal ends, the elongate anti-rotation sleeve being movably mounted to the elongate shaft and reciprocating relative thereto between a retracted position and an extended position, the distal end of the elongate anti-rotation sleeve including an anti-rotation member; and an actuation mechanism for controlling positioning and reciprocation of the elongate anti-rotation sleeve relative to the elongate shaft between the retracted and extended positions, and for locking the elongate anti-rotation sleeve relative to the elongate shaft.

Employing of the surgical tool includes: employing the engagement member at the distal end of the elongate shaft of the surgical tool to securely releasably engage the intervertebral device; employing the actuation mechanism of the surgical tool to position the elongate anti-rotation sleeve in the extended position to engage the intervertebral device, and to lock the elongate anti-rotation sleeve relative to the elongate shaft; inserting the intervertebral device between the vertebral members of the patient employing the surgical tool; releasing the engagement member at the distal end of the elongate shaft from engagement with the intervertebral device; and thereafter, retracting the anti-rotation member from engagement with the intervertebral device.

In the embodiments illustrated, the surgical tool further includes an impaction cap coupled to the proximal end of the elongate shaft, and the actuation mechanism locks the elongate anti-rotation sleeve relative to the elongate shaft notwithstanding impacting of the impaction cap during the inserting of the intervertebral device between the vertebral members of the patient. Further, in the embodiments illustrated, the engagement member comprises a threaded member sized to threadably engage a threaded opening in the intervertebral device. Thus, employing the engagement member includes threading the engagement member into the threaded opening of the intervertebral device. Further, employing the actuation mechanism of the surgical tool includes positioning the elongate anti-rotation sleeve in the extended position with the anti-rotation member mated within a corresponding anti-rotation opening within the intervertebral device.

Still further, the surgical tool may include threads disposed adjacent to the proximal end thereof, and the actuation mechanism may comprise a locking collar threadably engaging the threads of the elongate shaft and mechanically coupling to the proximal end of the elongate anti-rotation sleeve. In this tool embodiment, employing of the actuation mechanism includes threading the locking collar along the threads of the elongate shaft to position the elongate anti-rotation sleeve in the extended position and lock the elongate anti-rotation sleeve relative to the elongate shaft.

In another configuration outlined above, the actuation mechanism of the surgical tool includes at least one spring-biased latch mechanism, which is biased to lock the elongate anti-rotation sleeve relative to the elongate shaft. In this embodiment, employing of the actuation mechanism includes compressively engaging the at least one spring-biased latch mechanism to allow for reciprocation of the elongate anti-rotation sleeve relative to the elongate shaft between the retracted and extended positions, and releasing compressive engagement of the at least one spring-biased latch mechanism once in the extended position to allow the at least one spring-biased latch mechanism to lock the elongate anti-rotation sleeve relative to the elongate shaft in the extended position.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A surgical tool for positioning an intervertebral device between vertebral members, the surgical tool comprising:

an elongate shaft having proximal and distal ends defining a first longitudinal axis extending therebetween, the distal end of the elongate shaft comprising an engagement member adapted to releasably engage an intervertebral device;

an anti-rotation sleeve having proximal and distal ends, the anti-rotation sleeve being movably mounted to the elongate shaft and reciprocating relative thereto between a retracted position and an extended position, the distal end of the anti-rotation sleeve comprising an anti-rotation member;

an actuation mechanism for controlling positioning and reciprocation of the anti-rotation sleeve relative to the elongate shaft between the retracted position and the extended position and for locking the anti-rotation sleeve relative to the elongate shaft, wherein when the intervertebral device is releasably engaged by the engagement member at the distal end of the elongate shaft, and the anti-rotation sleeve is in the extended position, the anti-rotation member at the distal end of the anti-rotation sleeve engages the intervertebral device and prevents rotation of the intervertebral device when releasing the engagement member from engagement with the intervertebral device; and wherein the actuation mechanism comprises at least one spring-biased latch mechanism for locking the anti-rotation sleeve relative to the elongate shaft, and when compressively engaged, allows for reciprocation of the anti-rotation sleeve relative to the elongate shaft between the retracted and extended positions, the at least one spring-biased latch mechanism comprising at least one spring-biased latch member in spring-biased contact with the anti-rotation sleeve for locking the anti-rotation sleeve relative to the elongated shaft.

2. The surgical tool of claim 1, further comprising an impaction cap coupled to the proximal end of the elongate shaft, wherein the actuation mechanism locks the anti-rotation sleeve relative to the elongate shaft to prevent movement thereof during impacting of the surgical tool at the impaction cap, the elongate shaft being fixedly secured to the impaction cap and comprising a stepped out diameter at the proximal end thereof to facilitate accommodation of an impaction load imparted to the surgical tool by an impacting of the surgical tool at the impaction cap.

3. The surgical tool of claim 1, wherein the actuation mechanism further comprises an actuation cover fixedly mounted to the elongate shaft adjacent to the proximal end of the elongate shaft, the actuation cover including an axial opening aligned with the first longitudinal axis of the elongate shaft and sized to allow reciprocation of the proximal end of the anti-rotation sleeve within the actuation cover, and wherein the at least one spring-biased latch mechanism is mounted within the actuation cover and is biased to engage the anti-rotation sleeve, and thereby lock the anti-rotation sleeve relative to the elongate shaft.

4. The surgical tool of claim 1, further comprising a handle and impaction cap mounted to the proximal end of the elongate shaft, wherein the at least one spring-biased latch mechanism locks the anti-rotation sleeve relative to the elongate shaft notwithstanding impacting of the surgical tool at the impaction cap.

5. The surgical tool of claim 1, wherein the intervertebral device comprises a threaded opening and an anti-rotation opening offset therefrom, and wherein the engagement member comprises a threaded engagement member sized to threadably engage the threaded opening and the intervertebral device, and wherein the anti-rotation member is configured and sized to mate with the intervertebral device within the anti-rotation opening thereof when the intervertebral device is releasably engaged by the threaded engagement member and the anti-rotation sleeve is in the extended position.

6. The surgical tool of claim 5, wherein the intervertebral device comprises one of a circular, non-circular or oblong stabilization sphere, and wherein the anti-rotation member when mated with the anti-rotation opening of the intervertebral device prevents rotation of the intervertebral device between vertebral members when releasing the threaded engagement member from engagement with the threaded opening of the intervertebral device.

7. The surgical tool of claim 1, wherein the anti-rotation sleeve comprises an elongate anti-rotation sleeve, and wherein the proximal and distal ends thereof define a second longitudinal axis extending therebetween, wherein the second longitudinal axis of the anti-rotation sleeve is coaxial with the first longitudinal axis of the elongate shaft, and wherein the anti-rotation sleeve comprises a grip formed on an outer surface thereof to facilitate manual reciprocation of the anti-rotation sleeve relative to the elongate shaft when the at least one spring-biased latch mechanism is compressively engaged.

8. A surgical tool for positioning an intervertebral device between vertebral members, the surgical tool comprising:

an elongate shaft having proximal and distal ends defining a first longitudinal axis extending therebetween, the distal end of the elongate shaft comprising an engagement member adapted to releasably engage an intervertebral device;

an anti-rotation sleeve having proximal and distal ends, the anti-rotation sleeve being movably mounted to the elongate shaft and reciprocating relative thereto between a retracted position and an extended position, the distal end of the anti-rotation sleeve comprising an anti-rotation member;

an actuation mechanism for controlling positioning and reciprocation of the anti-rotation sleeve relative to the elongate shaft between the retracted position and the extended position and for locking the anti-rotation sleeve relative to the elongate shaft, wherein when the intervertebral device is releasably engaged by the engagement member at the distal end of the elongate shaft, and the anti-rotation sleeve is in the extended position, the anti-rotation member at the distal end of the anti-rotation sleeve engages the intervertebral device and prevents rotation of the intervertebral device when releasing the engagement member from engagement with the intervertebral device;

wherein the actuation mechanism comprises at least one spring-biased latch mechanism for locking the anti-rotation sleeve relative to the elongate shaft, and when compressively engaged, allows for reciprocation of the anti-rotation sleeve relative to the elongate shaft between the retracted and extended positions;

wherein the actuation mechanism further comprises an actuation cover fixedly mounted to the elongate shaft adjacent to the proximal end of the elongate shaft, the actuation cover including an axial opening aligned with the first longitudinal axis of the elongate shaft and sized to allow reciprocation of the proximal end of the anti-rotation sleeve within the actuation cover, and wherein the at least one spring-biased latch mechanism is mounted within the actuation cover and is biased to engage the anti-rotation sleeve, and thereby lock the anti-rotation sleeve relative to the elongate shaft; and wherein each latch mechanism of the at least one spring-biased latch mechanism comprises a spring-biased latch member pivotally mounted within the actuation cover, each latch member including a first end comprising an exposed button, and a second end configured to engage the anti-rotation sleeve within a groove in the proximal end of the anti-rotation sleeve, and wherein each latch mechanism further comprises spring-biasing of the latch member relative to the actuation cover so that the second end of the latch member resides within the groove in the proximal end of the anti-rotation sleeve and engages the anti-rotation sleeve to lock the anti-rotation sleeve relative to the elongate shaft.

9. The surgical tool of claim 8, wherein the groove in the proximal end of the anti-rotation sleeve has a length equal to the distance between the retracted and extended positions of the anti-rotation sleeve, and wherein application of a compressive force to the exposed button of each latch member allows an operator to control positioning of the second end of each latch member within the groove of the anti-rotation sleeve, and thereby control positioning of the anti-rotation sleeve relative to the elongate shaft.

10. The surgical tool of claim 9, wherein the engagement member at the distal end of the elongate shaft comprises a threaded member sized to threadably engage a threaded opening in the intervertebral device, and wherein the anti-rotation member comprises an anti-rotation pin configured and sized to mate to a corresponding anti-rotation opening within the intervertebral device to prevent rotation of the intervertebral device when releasing the engagement member from engagement with the intervertebral device.

11. A surgical tool for positioning an intervertebral device between vertebral members, the surgical tool comprising:

an elongate shaft having proximal and distal ends defining a first longitudinal axis extending therebetween, the distal end of the elongate shaft comprising a threaded engagement member adapted to releasably engage an intervertebral device;

an impaction cap physically connected to the proximal end of the elongate shaft, wherein impacting force applied to the impaction cap is transferred to the elongate shaft, and hence to the threaded engagement member at the distal end thereof, the elongate shaft being fixedly secured to the impaction cap and comprising a stepped out diameter at the proximal end thereof to facilitate accommodation of an impaction load imparted to the surgical tool by impacting of the surgical tool at the impaction cap;

an elongate anti-rotation sleeve having proximal and distal ends defining a second longitudinal axis extending therebetween, the second longitudinal axis of the elongate anti-rotation sleeve being coaxial with the first longitudinal axis of the elongate shaft, and wherein the elongate anti-rotation sleeve is movably mounted to the elongate shaft and reciprocates relative thereto between a retracted position and an extended position, the distal end of the elongate anti-rotation sleeve comprising an anti-rotation member; and an actuation mechanism for controlling positioning and reciprocation of the elongate anti-rotation sleeve relative to the elongate shaft between the retracted position and the extended position and for locking the elongate anti-rotation sleeve relative to the elongate shaft, wherein when the intervertebral device is releasably engaged by the threaded engagement member at the distal end of the elongate shaft, and the elongate anti-rotation sleeve is in the extended position, the anti-rotation member at the distal end of the elongate anti-rotation sleeve engages the intervertebral device and prevents rotation of the intervertebral device when releasing the threaded engagement member from engagement with the intervertebral device.

12. The surgical tool of claim 11, wherein the actuation mechanism comprises at least one spring-biased latch mechanism for locking the elongate anti-rotation sleeve relative to the elongate shaft, and when compressively engaged, allows for reciprocation of the elongate anti-rotation sleeve relative to the elongate shaft between the retracted and extended positions, wherein the actuation mechanism comprises at least one spring-biased latch mechanism for locking the anti-rotation sleeve relative to the elongate shaft, and when compressively engaged, allows for reciprocation of the anti-rotation sleeve relative to the elongate shaft between the retracted and extended positions, the at least one spring-biased latch mechanism comprising at least one sprig-biased latch member in spring-biased contact with the anti-rotation sleeve for locking the anti-rotation sleeve relative to the elongated shaft.

13. The surgical tool of claim 12, wherein the actuation mechanism further comprises an actuation cover fixedly mounted to the elongate shaft adjacent to the proximal end of the elongate shaft, the actuation cover including an axial opening aligned with the first longitudinal axis of the elongate shaft and sized to allow reciprocation of the proximal end of the elongate anti-rotation sleeve within the actuation cover, and wherein the at least one spring-biased latch mechanism is mounted within the actuation cover and is biased to engage the elongate anti-rotation sleeve, and thereby lock the elongate anti-rotation sleeve relative to the elongate shaft.

14. The surgical tool of claim 13, wherein each latch mechanism of the at least one spring-biased latch mechanism comprises a spring-biased latch member pivotally mounted within the actuation cover, each latch member including a first end comprising an exposed button, and a second end configured to engage the elongate anti-rotation sleeve within a groove in the proximal end of the elongate anti-rotation sleeve, and wherein each latch mechanism further comprises spring-biasing of the latch member relative to the actuation cover so that the second end of the latch member resides within the groove in the proximal end of the elongate anti-rotation sleeve and engages the anti-rotation sleeve to lock the elongate anti-rotation sleeve relative to the elongate shaft.

* * * * *